United States Patent
Goto

(10) Patent No.: US 9,526,643 B2
(45) Date of Patent: Dec. 27, 2016

(54) STENT, STENT DELIVERY DEVICE AND STENT DELIVERY METHOD

(71) Applicant: TERUMO KABUSHIKI KAISHA, Shibuya-ku (JP)

(72) Inventor: Hiroki Goto, Ashigarakami-gun (JP)

(73) Assignee: TERUMO KABUSHIKI KAISHA, Shibuya-Ku, Tokyo (JP)

( * ) Notice: Subject to any disclaimer, the term of this patent is extended or adjusted under 35 U.S.C. 154(b) by 363 days.

(21) Appl. No.: 14/026,257

(22) Filed: Sep. 13, 2013

(65) Prior Publication Data

US 2014/0018905 A1  Jan. 16, 2014

Related U.S. Application Data

(63) Continuation of application No. 12/412,159, filed on Mar. 26, 2009, now Pat. No. 8,556,959, which is a (Continued)

(30) Foreign Application Priority Data

Sep. 29, 2006  (JP) .................................. 2006-269201

(51) Int. Cl.
*A61F 2/86* (2013.01)
*A61F 2/90* (2013.01)
(Continued)

(52) U.S. Cl.
CPC . *A61F 2/90* (2013.01); *A61F 2/91* (2013.01); *A61F 2/915* (2013.01); *A61F 2/958* (2013.01); *A61F 2002/91558* (2013.01)

(58) Field of Classification Search
CPC .............. A61F 2/90; A61F 2/91; A61F 2/915; A61F 2/958; A61F 2002/91558
See application file for complete search history.

(56) References Cited

U.S. PATENT DOCUMENTS

| 5,104,404 A | 4/1992 | Wolff |
| 5,755,781 A | 5/1998 | Jayaraman |

(Continued)

FOREIGN PATENT DOCUMENTS

| EP | 1 428 549 A1 | 6/2004 |
| FR | 2 781 143 A1 | 1/2000 |

(Continued)

OTHER PUBLICATIONS

Korean Office Action (Notice of Preliminary Rejection) dated Sep. 27, 2013, issued by the Korean Patent Office in corresponding Korean Patent Application No. 10-2009-7006292, and English language translation of Office Action. (8 pages).

(Continued)

*Primary Examiner* — Julie A Szpira
(74) *Attorney, Agent, or Firm* — Buchanan Ingersoll & Rooney PC

(57) ABSTRACT

A stent to be implanted in a living body is formed substantially as a tube having a form in which plural wavy annular members are arranged adjacent to each other in the axial direction of the stent, with the axially adjacent wavy annular members connected to each other. The stent possesses an outer diameter whose dimension is so set that the stent is insertable into a lumen inside a living body, and is expandable when a force spreading radially from the inside of the tube is applied. The wavy annular member has parallel straight-line portions extending parallel to the axis of the stent before and after the stent expands. The stent has connection portions each connecting ends of the parallel straight-line portions of the adjacent wavy annular members to each other.

5 Claims, 13 Drawing Sheets

Related U.S. Application Data continuation of application No. PCT/JP2007/069406, filed on Sep. 27, 2007.

(51) Int. Cl.
*A61F 2/91* (2013.01)
*A61F 2/915* (2013.01)
*A61F 2/958* (2013.01)

(56) References Cited

U.S. PATENT DOCUMENTS

| | | | |
|---|---|---|---|
| 6,066,168 A | | 5/2000 | Lau et al. |
| 2002/0007212 A1* | | 1/2002 | Brown ............... A61F 2/91 623/1.16 |
| 2002/0177893 A1* | | 11/2002 | Brown ............... A61F 2/91 623/1.16 |
| 2002/0198593 A1* | | 12/2002 | Gomez ............... A61F 2/91 623/1.16 |
| 2003/0014102 A1* | | 1/2003 | Hong ............... A61F 2/91 623/1.15 |
| 2004/0044400 A1 | | 3/2004 | Cheng et al. |
| 2004/0106985 A1 | | 6/2004 | Jang |
| 2005/0015136 A1* | | 1/2005 | Ikeuchi ............... A61F 2/91 623/1.15 |
| 2005/0015139 A1 | | 1/2005 | Brown et al. |
| 2005/0070991 A1* | | 3/2005 | Pienknagura ....... A61F 2/915 623/1.11 |
| 2005/0131530 A1 | | 6/2005 | Darack |
| 2006/0224229 A1 | | 10/2006 | Goto |
| 2006/0235506 A1 | | 10/2006 | Ta et al. |
| 2007/0050011 A1* | | 3/2007 | Klein ............... A61F 2/91 623/1.16 |
| 2007/0055353 A1* | | 3/2007 | Fliedner ............... A61F 2/91 623/1.16 |
| 2007/0100434 A1* | | 5/2007 | Gregorich ............... A61F 2/91 623/1.16 |
| 2010/0256739 A1* | | 10/2010 | Tippett ............... A61F 2/91 623/1.16 |

FOREIGN PATENT DOCUMENTS

| | | |
|---|---|---|
| JP | 10-503676 A | 4/1998 |
| JP | 2002-136601 A | 5/2002 |
| JP | 2003-19208 A | 1/2003 |
| JP | 2003-62084 A | 3/2003 |
| JP | 2006-520239 A | 9/2006 |
| JP | 2006-305341 A | 11/2006 |
| WO | WO 96/03092 A1 | 2/1996 |
| WO | WO 00/03661 A1 | 1/2000 |
| WO | WO 02/060344 A2 | 8/2002 |
| WO | 2004058105 A2 | 7/2004 |

OTHER PUBLICATIONS

Office Action (Notice of Preliminary Rejection) issued on Oct. 2, 2014, by the Korean Intellectual Property Office in corresponding Korean Patent Application No. 10-2014-7016968, and an English translation of the Office Action. (6 pages).

International Search Report (PCT/ISA/210) dated Nov. 21, 2007.

European Search report issued Oct. 22, 2012 by the European Patent Office in corresponding European Application No. 07829145.7.

Communication pursuant to Article 94(3) EPC issued Jun. 17, 2013 by the European Patent Office in European Patent Application No. 07 829 145.7.

Office Action (Notice of Final Rejection) issued on Mar. 28, 2014, by the Korean Intellectual Property Office in corresponding Korean Patent Application No. 10-2009-7006292. (3 pages).

Extended European Search Report issued on Dec. 11, 2015, by the European Patent Office in corresponding European Application No. 15194468.3 (7 pages, in English).

* cited by examiner

STENT, STENT DELIVERY DEVICE AND STENT DELIVERY METHOD

TECHNICAL FIELD

This application is a continuation of U.S. application Ser. No. 12/412,159 filed on Mar. 26, 2009 which is a continuation of International Application No. PCT/JP2007/069406 filed on Sep. 27, 2007, and claims priority to Japanese Application No. 2006-269201 filed on Sep. 29, 2006, the entire content of all three of which is incorporated herein by reference.

TECHNOLOGICAL FIELD

The present invention relates to a stent that is implanted in lumens of a living body such as the blood vessel, the bile duct, the trachea, the esophagus, the ureter, and the like to improve a stenosed portion or a closed portion generated in the lumens. The present invention also relates to a stent delivery device and stent delivery method.

BACKGROUND DISCUSSION

To cure various diseases caused when blood vessels or lumens are stenosed or closed, the stent is a tubular medical appliance to be implanted in lumens of the living body to expand the stenosed or closed portion and thereby secure the passage.

The stent is inserted into the body from the outside. Therefore the stent is so constructed that its diameter is relatively small when it is inserted into the body and is enlarged at a desired stenosed or closed portion by expanding the stent. The stent then maintains the expanded state to keep the lumen open.

The stent is cylindrical and made of a metal wire or a processed metal pipe. After the stent is mounted on a catheter or the like and the diameter of the stent is decreased, the stent is inserted into the body. Thereafter, the stent is expanded at the desired portion or location by using an expanding method and is fixed to the inner wall of the lumen of the desired portion, with the stent in close contact with the lumen inner wall to maintain the configuration of the lumen. Stents are classified into self-expandable stents and balloon expandable stents, depending upon the function of the stent and the implantation method. The balloon expandable stent, which has no self-expanding function or capability, is located at a desired portion. Then, a balloon positioned inside the stent is inflated to outwardly expand (plastically deform) the stent by an expansive force of the balloon so that the stent is fixed to the inner surface of the desired lumen with the stent in close contact with the lumen inner surface. Thus, to implant this type of stent to the desired portion of the living body, It is necessary to perform an operation of expanding the stent. The balloon expandable stent is primarily used as the stent to cure blood vessels and particularly the coronary arteries. The stent must have an axially flexible construction to cope with a variety of situations.

Balloon expandable stents are classified into closed cell types and opened cell types, depending on the configuration of the strut of the stent. The balloon expandable stent of the opened cell type is advantageous in that it is flexible. Thus the balloon expandable stent of the opened cell type can be favorably implanted in a desired portion because it is capable of flexibly following a travel direction (direction of extent) of a blood vessel and its configuration. Thereby it is possible to prevent the blood vessel from being stimulated.

But the balloon expandable stent of the opened cell type has the disadvantage that the stratum of the stent flares outwardly. On the other hand, the balloon expandable stent of the closed cell type is advantageous in that the stratum of the stent does not flare outwardly. However, this type of stent suffers from the disadvantage that it is incapable of flexibly following the travel direction or direction of extent of the blood vessel and its configuration. Thus, balloon expandable stents of the opened cell type and the closed cell type have both advantages and disadvantages. Thus it is necessary to use the balloon expandable stent of the opened cell type or the closed cell type depending upon the direction of extent and the configuration of the blood vessel.

An example of the balloon expandable stent of the opened cell type is disclosed in Japanese Patent Application Laid-Open No. 2002-136601.

An example of a closed cell-type balloon expandable stent is disclosed in International Application Publication No. WO 96/03092 and Japanese Patent Application Laid-Open No. 10-503676 which corresponds to in International Application Publication No. WO 96/03092.

But in this closed cell-type stent, connection portions are disposed all over the stent. Thus this stent lacks flexibility and has a construction not well suited for following the inside of a blood vessel and being disposed at a curved portion.

In the balloon expandable stent of the opened cell type disclosed in Japanese Patent Application Laid-Open No. 2002-136601, the opened cell portion has a certain expanded-state retention force. However, it is desirable that the stent have a higher expanded-state retention force. It is also desirable that the stent have a low degree of a length change in its axial direction when it expands and has a higher follow-up performance for organs.

It is desirable that a living body-implantable stent possess a relatively low degree of axial length change during expansion, a relatively high follow-up performance for organs and a relatively high expanded-state retention force.

SUMMARY

A stent is formed substantially as a tube having a form in which plural wavy annular members are arranged adjacent to each other in an axial direction of the stent with the adjacent wavy annular members connected to each other. The stent has a diameter whose dimension is so set that the stent can be inserted into a lumen inside a living body. The stent can be expanded when a force spreading radially from an inside of the tube is applied thereto. The wavy annular member has parallel straight-line portions extended in parallel with the axis of the stent before and after the stent expands. The stent has connection portions each connecting opposed ends of the parallel straight-line portions of the adjacent wavy annular members to each other.

According to another aspect, a stent comprises a plurality of wavy annular members arranged axially adjacent one another along an axial extent of the stent to form a tubular-shaped stent, wherein the stent is expandable from a first state of a first size permitting the stent to be positioned in a lumen of a living body to an expanded second state of a second size larger than the first size upon application of a radially outwardly directed expansion force from inside the stent. The wavy annular members comprise a first wavy annular member, a second wavy annular member axially adjacent the first wavy annular member without any other wavy annular member positioned between the first and second wavy annual members, and a third wavy annular member axially adjacent the second wavy annular member without any other wavy annular member positioned between the second and third wavy annual members. The first, second and third wavy annular members each comprise a plurality of straight line portions positioned parallel to the axis of the stent when the stent is in both the first state and the expanded second state, and a plurality of additional portions angled with respect to one another, with the plurality of straight line portions and the plurality of additional portions being interconnected so that each of the first, second and third wavy annular members is a continuous wavy annular member. A first connection portion connects one of the straight line portions of the first wavy annular member to one of the straight line portions of the second wavy annular member, a second connection portion connects another one of the straight line portions of the first wavy annular member to another one of the straight line portions of the second wavy annular member, a third connection portion connects one of the straight line portions of the second wavy annular member to one of the straight line portions of the third wavy annular member, and a fourth connection portion connects another one of the straight line portions of the second wavy annular member to another one of the straight line portions of the third wavy annular member. The first and second connection portions are circumferentially offset from one another, and the third and fourth connection portions being circumferentially offset from one another. In addition, the third and fourth connection portions are not aligned with the first and second connection portions in the axial direction of the stent.

A stent delivery device comprises a tubular shaft body; a balloon, foldable and expandable, which is disposed at a distal end of the shaft body; and a stent which is mounted on the folded balloon, with the stent covering the balloon and being expandable owing to expansion of the balloon. The stent described above is preferably used with the stent delivery device.

BRIEF DESCRIPTION OF DRAWING FIGURES

DETAILED DESCRIPTION

Figure 1:
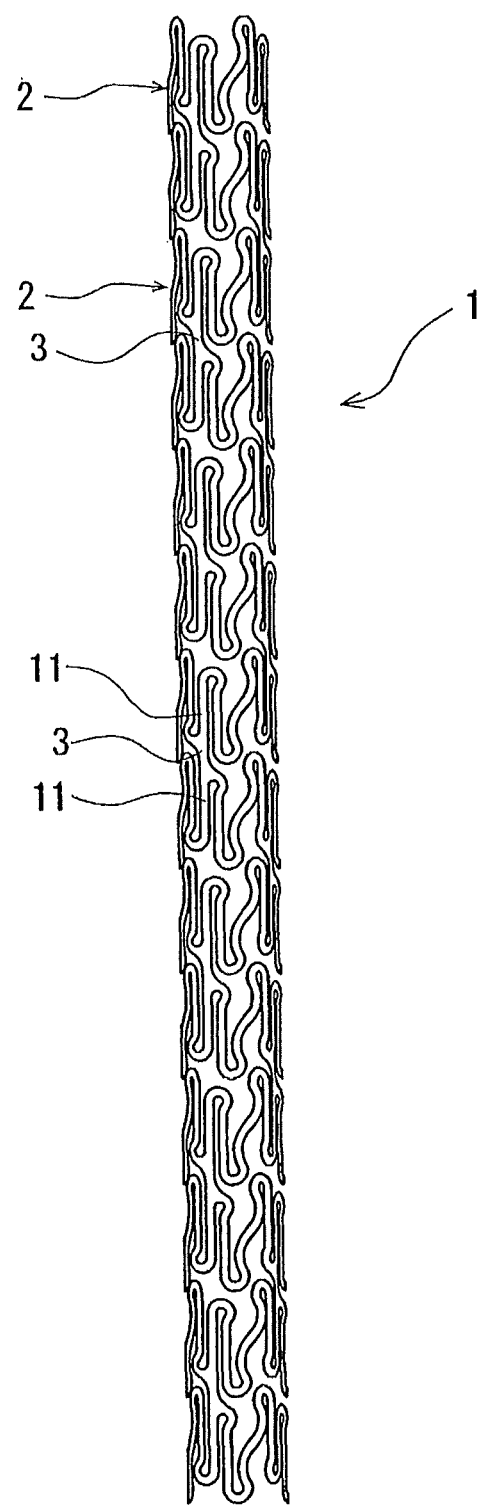
FIG. 1 is a front view of one embodiment of a stent disclosed here that is to be implanted in a living body.

The stent disclosed by way of example in several embodiments described bellow and illustrated by way of the drawing figures is sized and configured to be implanted in a living body.

Referring to FIG. 1, a stent 1 according to one embodiment disclosed here is substantially tubular in form or shape. Generally speaking, the stent is comprised of a plurality of wavy annular members 2 arranged adjacent one another in the axial direction of the stent 1, with the axially adjacent wavy annular members 2 connected to each other. The stent possesses a diameter dimensioned so set that the stent 1 can be inserted into a lumen inside a living body, and can be expanded when a force spreading radially from the inside of the tube is applied to the stent. Each wavy annular member 2 includes a plurality of straight-line portions 11 extending in parallel with the axis of the stent 1 before and after the stent 1 expands. The straight-line portions 11 in each wavy annular member 2 are parallel to one another and to the straight-line portions 1 in the other wavy annular members 2. The stent 1 also includes a plurality of connection portions 3 each connecting together the ends of parallel straight-line portions 11 of axially adjacent wavy annular members 2.

As mentioned, the stent 1 is tubular-shaped and dimensioned so that its outer diameter allows the stent 1 to be inserted into a lumen inside a living body. Also, the stent 1 is adapted to be expanded outwardly when a radially outwardly spreading force is applied to the stent from the inside of the tubular stent. The stent 1 is thus a so-called balloon expandable stent.

Figure 2:
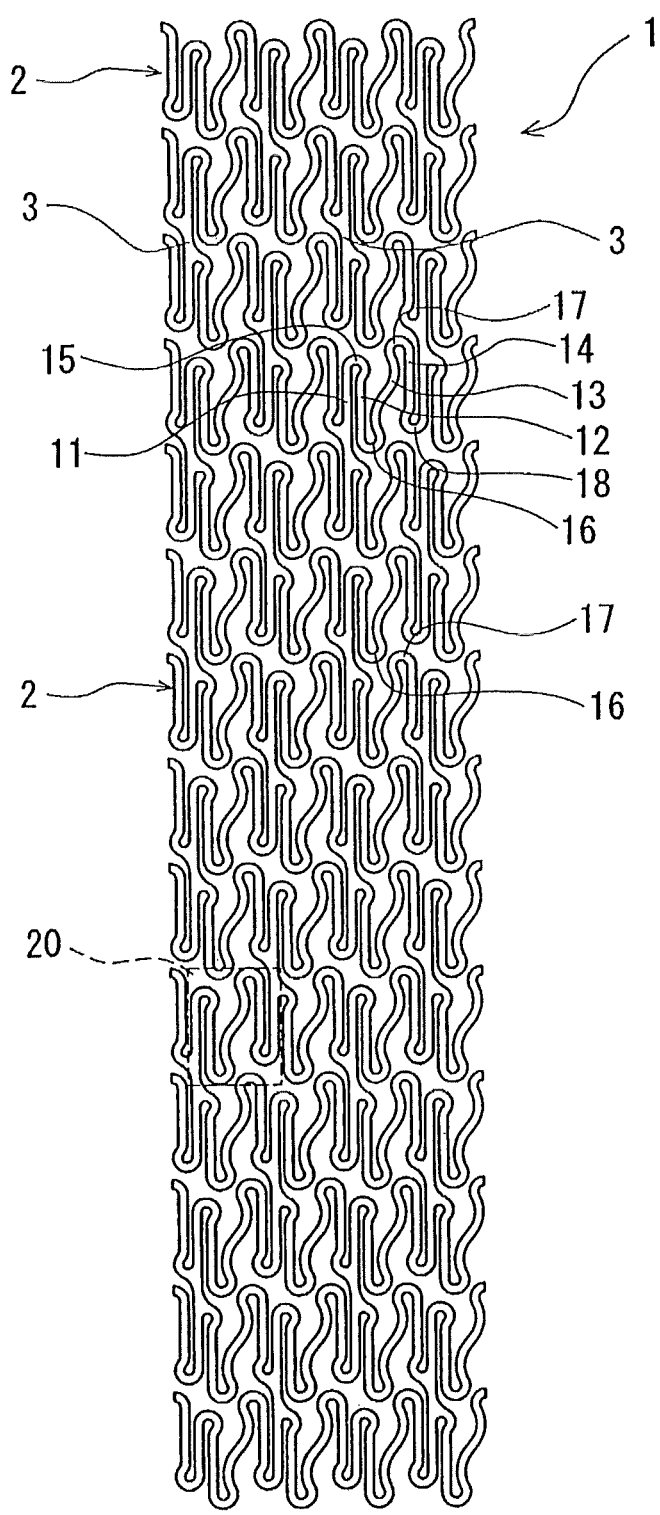
FIG. 2 is a development view, in plan view, of the stent shown in FIG. 1 illustrating the stent cut or separated along its length and laid out flat.

The stent 1 shown in FIGS. 1 and 2 includes, as mentioned previously, a plurality of axially adjacent wavy annular members 2, with the adjacent wavy annular members directly connected to each other. The number of wavy annular members 2 forming the stent 1 shown in FIGS. 1 through 5 is fourteen (14). However, the stent is not limited in this regard. The number of wavy annular members 2 is different depending upon the length of the stent and is preferably in the range of 4 to 50, more preferably 10 to 35. Each of the wavy annular members 2 includes a plurality of one-end side bent portions 15, 17 each having an apex at one-end side of the wavy annular member 2 in the axial direction, and a plurality of other-end side bent portions 16, 18 each having an apex at the other-end side of the wavy annular member 2 in the axial direction.

Thus, one-end side of each wavy annular member includes a plurality of circumferentially spaced apart bent portions 15 and a plurality of circumferentially spaced apart bent portions 17, with one of the bent portions 15 positioned circumferentially between each pair of adjacent bent portions 17, and with one of the bent portions 17 positioned circumferentially between each pair of adjacent bent portions 15. Similarly, the other-end side of each wavy annular member includes a plurality of circumferentially spaced apart bent portions 16 and a plurality of circumferentially spaced apart bent portions 18, with one of the bent portions 16 positioned circumferentially between each pair of adjacent bent portions 18, and with one of the bent portions 18 positioned circumferentially between each pair of adjacent bent portions 16. In the illustrated embodiment, the bent portions 17 extend further axially away from the other-end side of the wavy annular member than the bent portions 15. Likewise, the bent portions 16 extend further axially away from the one-end side of the wavy annular member than the bent portions 18.

Each of the wavy annular members 2 is composed of an annularly continuous or endless wavy line element. As mentioned, the one-end side bent portions 15, 17 are arranged in an alternating manner around the circumference of the wavy annular member. Similarly, the other-end side bent portions 16, 18 are arranged in an alternating manner around the circumference of the wavy annular member. The number of one-end side bent portions 15, 17 in each wavy annular member 2 is equal to the number of other-end side bent portions 16, 18.

In the embodiment shown in FIGS. 1-4, the total number of one-end side bent portions 15, 17 in each wavy annular member 2 is eight. Likewise, the total number of other-end side bent portions 16, 18 in each wavy annular member 2 is also eight. The stent is not necessarily limited in this regard as the number of one-end side bent portions of each wavy annular member 2 is preferably in the range of 4-12, more preferably 6-10, while the number of other-end side bent portions in each wavy annular member 2 is preferably in the range of 4-12, more preferably 6-10. The length of the wavy annular member 2 in the axial direction of the stent is preferably in the range of 0.5 mm to 2.0 mm, more preferably 0.9 mm to 1.5 mm.

Figure 3:
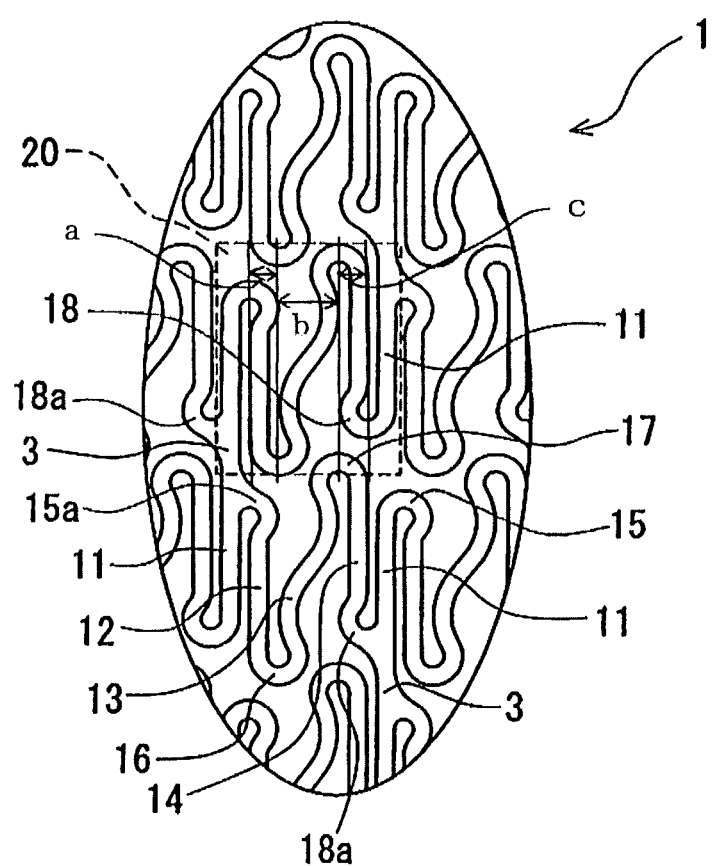
FIG. 3 is an enlarged plan view of a part of the stent shown in FIG. 2.
Figure 4:
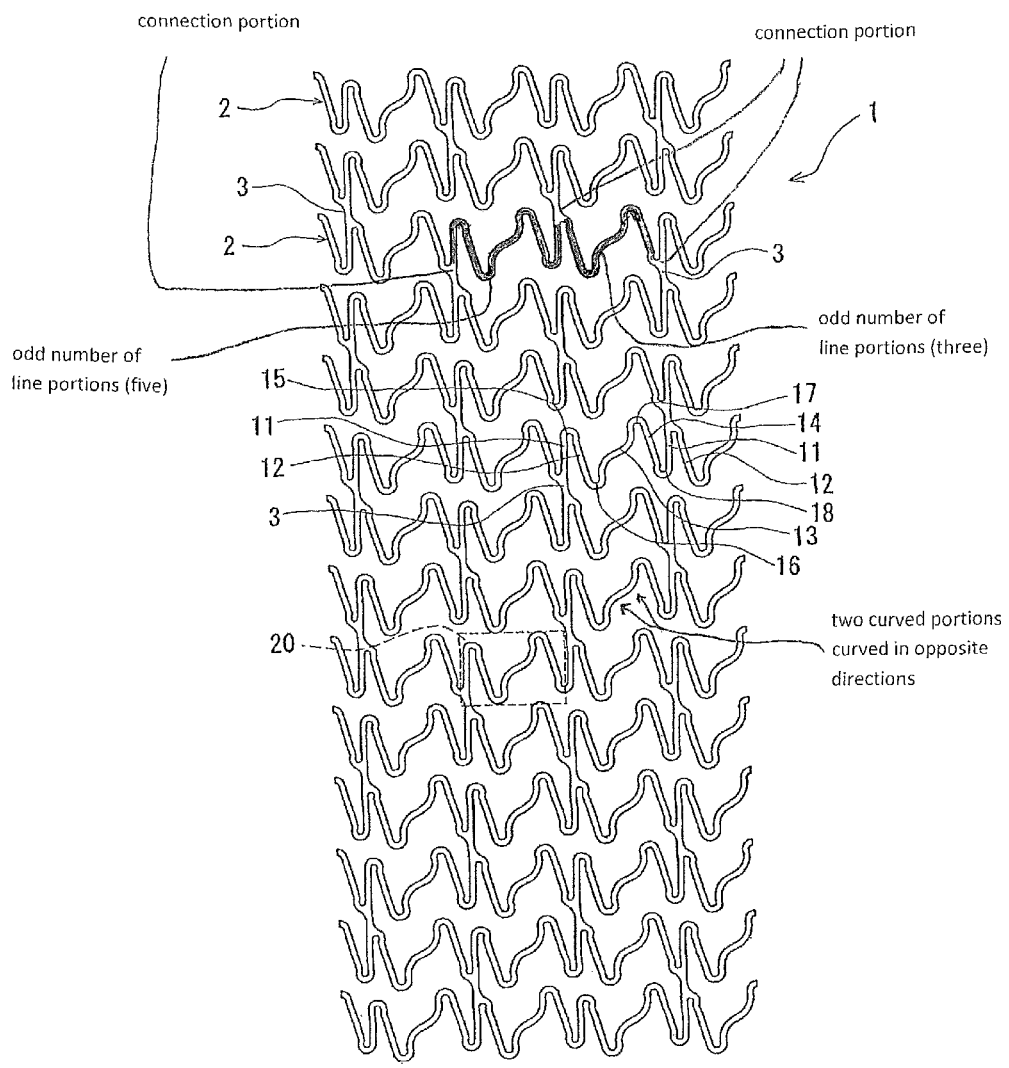
FIG. 4 is a development view, in plan view, of the stent shown in FIG. 1 at the time when the stent is manufactured.

As shown in FIGS. 1-4, the wavy annular member 2 includes a plurality of modified M-shaped linear portions 20, continuous with each other, each of which has four linear portions. The four linear portions are composed of: a parallel straight-line portion 11; a first inclined straight-line portion 12 connected to one end of the parallel straight-line portion 11 through the bent portion 15 (15a) and oriented oblique to the axis of the stent 1 at a predetermined angle at least when the stent 1 expands such as shown in FIG. 4; an inclined linear portion (in this embodiment, an inclined curved line portion) 13 connected to one end of the first inclined straight-line portion 12 through the bent portion 16 and extending obliquely at a predetermined angle to the axis of the stent; and a second inclined straight-line portion 14 connected to one end of the inclined curved line portion 13 through the bent portion 17 and oriented oblique to the axis of the stent 1 at a predetermined angle at least when the stent 1 expands as illustrated in FIG. 4. Each of the wavy annular members 3 includes a plurality of the modified M-shaped linear portions 20 positioned circumferentially adjacent tone another. The adjacent modified M-shaped linear portions 20 are connected by the bent portion 18 (18a) directly connecting one end of the second inclined straight-line portion 14 and the other end of the parallel straight-line portion 11 with each other, thus constructing the endless wavy annular member 2. Therefore it is possible to restrain the wavy annular member 2 from shortening in the axial length when the stent expands and impart a sufficient expanded-state retention force to the wavy annular member 2.

Figure 5:
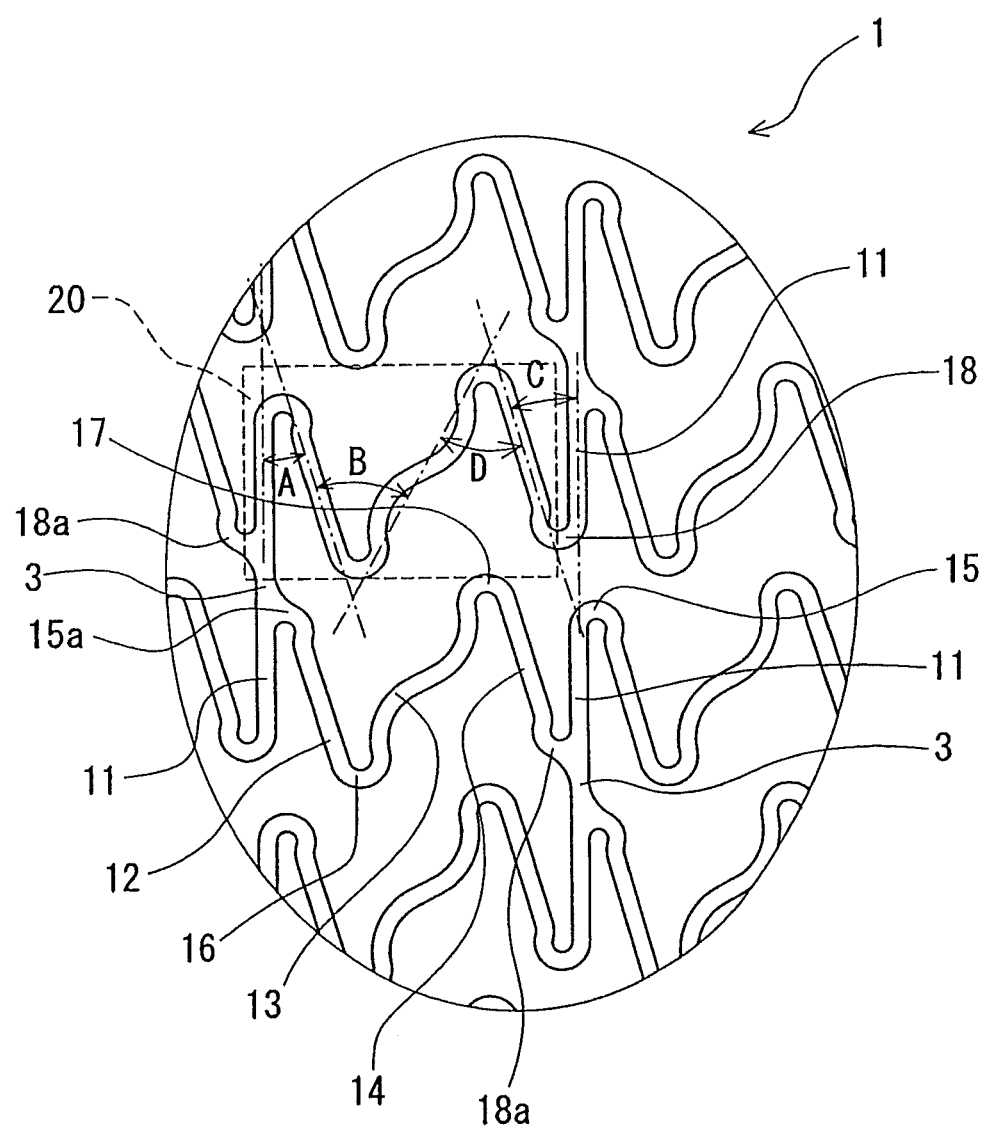
FIG. 5 is an enlarged view of a part of the stent shown in FIG. 4.

In this embodiment of the stent 1 as shown in FIG. 3 (before the stent expands, while the stent is compressed) and FIG. 5 (at a stent-manufacturing time and at a stent-expanding time), the wavy annular members 2 each include a plurality of the modified M-shaped linear portions 20, continuous with each other, each of which has the four linear portions composed of: the parallel straight-line portion 11; the first inclined straight-line portion 12 having a first end connected to a second end of the parallel straight-line portion 11 through the bent portion 15 (15a), arranged substantially parallel (before the stent expands) with the axis of the stent, and taking on an oblique orientation to the axis of the stent 1 at a predetermined angle when the stent 1 expands; the inclined curved line portion 13 having a first end connected to the second end of the first inclined straight-line portion 12 through the bent portion 16 and extending obliquely at a predetermined angle to the axis of the stent; and the second inclined straight-line portion 14 having a first end connected to the second end of the inclined curved line portion 13 through the bent portion 17, arranged almost parallel (before the stent expands) with the axis of the stent, and taking on an oblique orientation to the axis of the stent 1 at a predetermined angle when the stent 1 expands. The first inclined straight-line portion 12 and the second inclined straight-line portion 14 are almost parallel with the axis of the stent 1 before the stent expands, in other words when the stent is compressed. Therefore when the stent is compressed, it is possible to make the outer diameter of the stent relatively small. As illustrated in FIG. 4, when the stent is expanded, the parallel straight-line portion 11 of each wavy annular member remains oriented parallel to the axis of the stent, while the first inclined straight-line portion 12, the inclined curved line portion 13 and the second inclined straight-line portion 14 are oriented at an oblique angle relative to the stent axis (i.e., are other than parallel to the axis of the stent).

More specifically, as shown in FIGS. 3 and 5, the first inclined straight-line portion 12 and the second inclined straight-line portion 14 are almost parallel with the axis of the stent before the stent expands. When the stent expands, the first inclined straight-line portion 12 and the second inclined straight-line portion 14 extend in the same direction obliquely to the axis of the stent 1. In the stent 1 of this embodiment, when the stent expands, the first inclined straight-line portion 12 and the second inclined straight-line portion 14 extend obliquely to the axis of the stent and are almost parallel with each other. The inclined curved line portion 13 extends obliquely to the axis of the stent even before the stent is expanded (i.e., in the non-expanded position of the stent). When the stent expands, the inclined curved line portion 13 extends obliquely to the axis of the stent in a direction different from the direction in which the first inclined straight-line portion 12 and the second inclined straight-line portion 14 extend.

The number of one-end side bent portions and other-end side bent portions in each of the modified M-shaped linear portions 20 is two respectively as shown in FIGS. 1-4. Referring to FIG. 3, the separation distance b (in other words, the width of the modified M-shaped linear portion 20 in the inclined curved line portion 13) between the other-end side bent portion 16 and the one-end side bent portion 17 in the direction orthogonal to the axis of the stent 1 is larger than the separation distance a (in other words, the width of the modified M-shaped linear portion 20 in the first inclined straight-line portion 12) between the one-end side bent portion 15 and the other-end side bent portion 16 in the direction orthogonal to the axis of the stent 1, and is larger than the separation distance c (in other words, the width of the modified M-shaped linear portion 20 in the second inclined straight-line portion 14) between the one-end side bent portion 17 and the other-end side bent portion 18 in the direction orthogonal to the axis of the stent 1. With this arrangement, a sufficient expanded-state retention force is imparted to the wavy annular member 2. It is of course understood that the above references to the separation distance between the bent portions refers to the distance between the noted bent portions as measured from similar points on the bent portions, for example the width-wise center of the apex of the bent portion.

As mentioned above, and as shown in FIG. 3, in the wavy annular member 2, the bent portion 17 disposed at the one-end side of the inclined curved line portion 13 projects to a greater extent than the other one-end side bent portion 15 toward the one-end side in the axial direction of the stent. Similarly, the bent portion 16 disposed at the other-end side of the inclined curved line portion 13 projects to a greater axial extent than the other other-end side bent portion 18 toward the other-end side in the axial direction of the stent.

In the stent 1 of this embodiment, each wavy annular member 2 is composed of four modified M-shaped linear portions 20 which are successively arranged in the circumferential direction and connected together. The stent is not necessarily limited in this regard. It is preferable that each wavy annular member 2 is composed of three to five modified M-shaped linear portions 20.

At the time of the compression of the stent, each of the wavy annular members 2 includes a plurality of the one-end side bent portions 15, 17 each having the apex at the one-end side of the stent 1 in the axial direction, and a plurality of the other-end side bent portions 16, 18 each having the apex at the other-end side of the stent 1 in the axial direction. The apex of at least one of the one-end side bent portions 17 of the wavy annular member 2 penetrates to some extent into a space formed between the other-end side bent portions 16 of the adjacent wavy annular member 2. More specifically, the apex of at least one of the one-end side bent portions 17 of each wavy annular member 2 extends beyond a line connecting the end surface of the apexes of two of the other-end side bent portions 16 of the adjacent wavy annular member 2. Similarly the apex of at least one of the other-end side bent portion 16 of the wavy annular member 2 penetrates to some extent into a space formed between the one-end side bent portions 17 of the axially adjacent wavy annular member 2. That is, the apex of at least one of the other-end side bent portions 16 of each wavy annular member 2 extends beyond a line connecting the end surface of the apexes of two of the one-end side bent portions 17 of the axially adjacent wavy annular member 2. Therefore, the wavy annular member 2 has a sufficient expanded-state retention force at the time of the expansion.

It is preferable that the length of the parallel straight-line portion 11 is shorter than that of the first inclined straight-line portion 12, the inclined curved line portion 13, and the second inclined straight-line portion 14. By making the length of the parallel straight-line portion 11 relatively short, the expanded-state retention force can be enhanced.

It is preferable that the bent portion 15 (15a) connecting the parallel straight-line portion 11 of the wavy annular member 2 and the first inclined straight-line portion 12 to each other is rounded. This arrangement helps disperse strain at the time of the expansion and secure a higher safety rate. It is preferable that not only the bent portion 15 (15a) connecting one end of the parallel straight-line portion 11 of the wavy annular member 2 and the first inclined straight-line portion 12 to each other is rounded, but also that the bent portion 18 (18a) connecting the other end of the parallel straight-line portion 11 of the wavy annular member 2 and the second inclined straight-line portion 14 to each other is rounded. This also helps disperse a strain at the time of the expansion and secure a higher safety rate. It is preferable that the other bent portions 16, 17 are also rounded.

Figure 6:
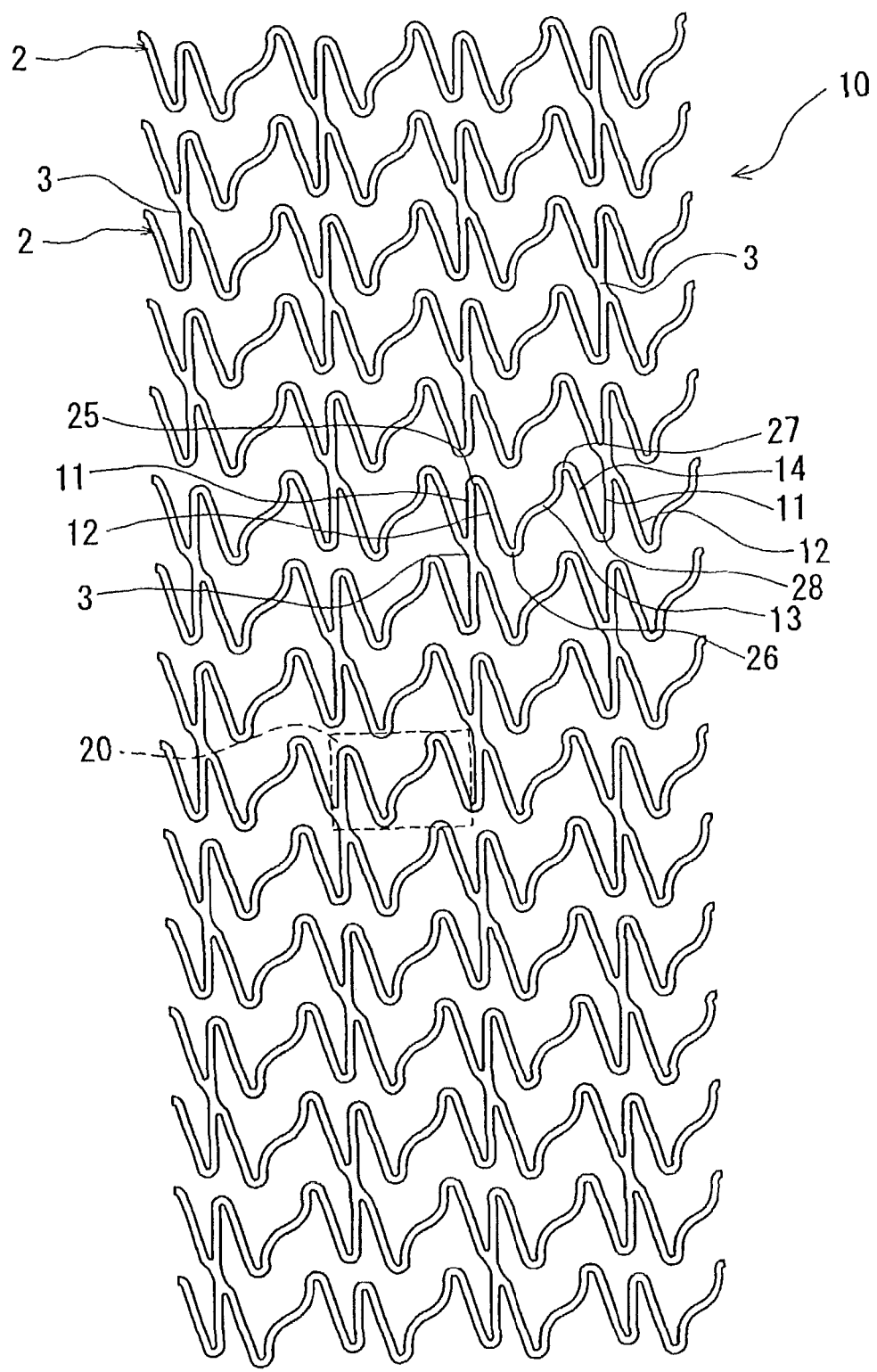
FIG. 6 is a development view, in plan, of a stent according to another embodiment disclosed here when the stent is manufactured.
Figure 7:
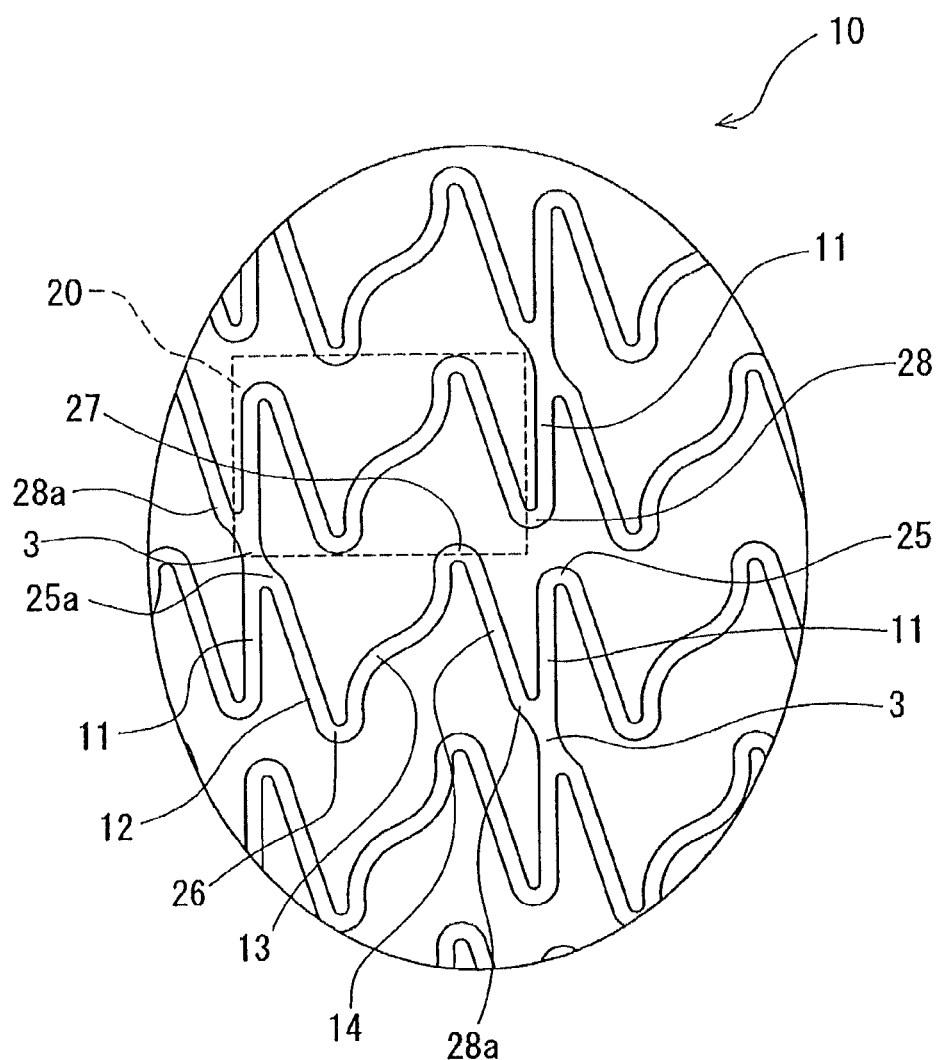
FIG. 7 is an enlarged view of a part of the stent shown in FIG. 6.

As described above, it is preferable that the above-described bent portions are rounded. The configuration of the bent portions is not limited to the described and illustrated configuration. It is possible that the bent portions are not rounded, as in the case of a stent 10 shown in FIGS. 6 and 7. The stent 10 shown in FIGS. 6 and 7 is different from the above-described stent 1 in the configuration of the above-described bent portions and the number of the wavy annular members 2. By not rounding the bent portions in the same manner shown in FIGS. 1-4, it is possible to make the outer diameter relatively small at the time of compression of the stent, thus further facilitating insertion of the stent into a small-diameter organ (for example, blood vessel) inside a living body.

As shown in FIG. 5, at the time of manufacturing the stent (the stent is preferably manufactured in the expanded state and is subsequently contracted after placement on the balloon), it is preferable that the ratio (B/A) of the internal angle B between the first inclined straight-line portion 12 and the inclined curved line portion 13 to the internal angle A between the parallel straight-line portion 11 and the first inclined straight-line portion 12 is not less than 1.8 (i.e., the ratio B/A is greater than or equal to 1.8). By setting the ratio (B/A) in this manner, the wavy annular member 2 has a sufficient expanded-state retention force at the time of the expansion. More preferably, the ratio (B/A) of the internal angle B to the internal angle A is 1.8 to 2.5.

With continued reference to FIG. 5, at the time of manufacturing the stent (at the expansion time of the stent), it is preferable that the ratio (D/C) of the internal angle D between the second inclined straight-line portion 14 and the inclined curved line portion 13 to the internal angle C between the parallel straight-line portion 11 and the second inclined straight-line portion 14 is not less than 1.8 (i.e., the ratio D/C is greater than or equal to 1.8). By setting the ratio (D/C) in this manner, the wavy annular member 2 has a sufficient expanded-state retention force at the time of the expansion. More preferably, the ratio (D/C) of the internal angle D to the internal angle C is 1.8 to 2.5.

In the stent 1 of this embodiment, the apexes of the one-end side bent portions 15 of axially successive and adjacent wavy annular members 2 are aligned with one another. Also, the apexes of the one-end side bent portions 17 of axially successive and adjacent wavy annular members 2 are aligned with one another. Similarly, the apexes of the other-end side bent portions 16 of axially successive and adjacent wavy annular members 2 are aligned with one another, and the apexes of the other-end side bent portions 18 of axially successive and adjacent wavy annular members 2 are aligned with one another. The axially adjacent wavy annular members 2 are connected to each other by the connection portions 3. In the stent 1 of this embodiment, ends of the parallel straight-line portions 11 of the axially adjacent wavy annular members 2 are proximate to each other and connected to each other with the short connection portions 3. Therefore the distance between the adjacent wavy annular members 2 is short, which greatly reduces the formation of a portion having a low expansive force.

In the stent 1 of this embodiment, as shown in FIGS. 1-4, two parallel straight-line portions 11 connected to each other with the connection portion 3 are almost aligned to each other. Therefore it is possible to prevent the stent from being shortened between the adjacent wavy annular members when the stent expands. The stent 1 has a plurality of the connection portions 3 connecting the axially adjacent wavy annular members to each other. Therefore the adjacent wavy annular members are not accidentally spaced from each other, which allows the entire stent to display a sufficient expansive force. More specifically, as shown in FIGS. 3 and 5, in the axially adjacent wavy annular members 2, the bent portion 18a connecting the other end of the parallel straight-line portion 11 and the second inclined straight-line portion 14 to each other, and the bent portion 15a connecting the one end of the parallel straight-line portion 11 and the first inclined straight-line portion 12 to each other are connected to each other with the short connection portion 3. In other words, the axially adjacent wavy annular members 2 are connected to each by way of the short connection portions 3 that directly interconnect the bent portion 18a of one wavy annular member and the bent portion 15 of an axially adjacent wavy annular member. Two parallel straight-line portions 11 connected to each other with the connection portion 3 are continuously aligned to each other.

In this embodiment, there is no portion where not less than two (in other words, three or more) parallel straight-line portions 11 axially continuous with each other are connected and integrated with each other with the connection portion. That is, the connection portion 3 connects only two parallel straight-line portions 11 to each other, and there is no portion of the stent where three parallel straight-line portions 11 are integral with each other. In other words, the stent is configured to avoid the possibility of the parallel straight-line portion 11 of three axially successive wavy annular members being aligned along a straight line. Therefore a load generated when one wavy annular member has changed its configuration to follow the deformation of a blood vessel can be prevented from being directly (or linearly) transmitted to an unadjacent wavy annular member, thus allowing the wavy annular members to display an expansion function individually.

Variations on the above-described arrangement are possible. For example, as with the stent 40 shown in FIG. 10, the stent can be configured so that only the ends of the stent 40 are provided with a portion where three axially continuous parallel straight-line portions 11 are connected and integral with each other through the use of two axially successive connection portions 3. By so doing, it is possible to enhance the strength (expanded-state retention force) of both ends of the stent.

Figure 10:
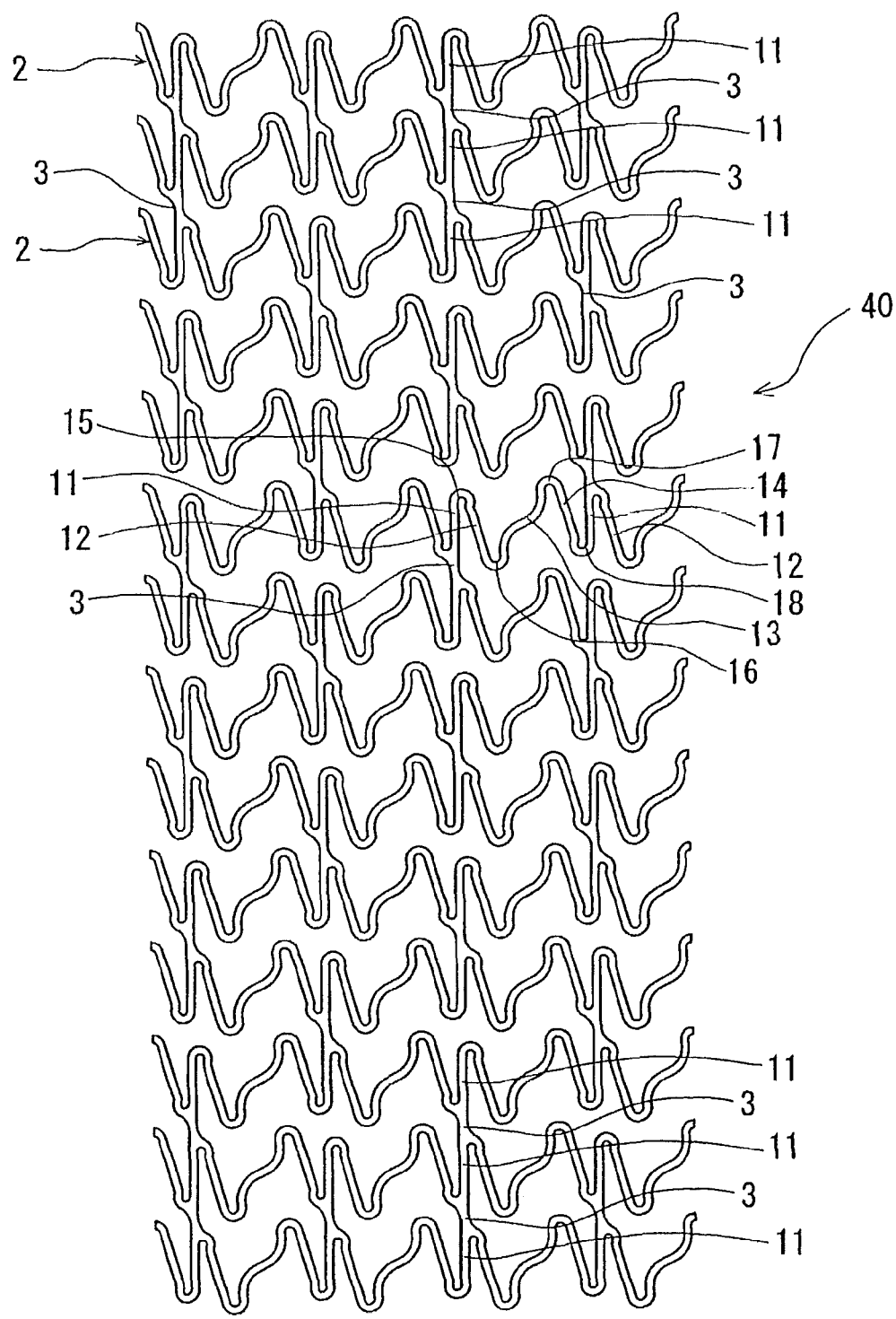
FIG. 10 is a development view, in plan, of a stent according to another embodiment disclosed here when the stent is manufactured.

Describing features of the stent shown in FIG. 10 in more detail, each end of the stent 40 includes four portions (instances) in which the straight-line portions 11 of the two axially adjacent wavy annular members 2 are connected and integrated with each other by the connection portions 3. Thus, four of the straight-line portions 11 in the end-most wavy annular member at one end of the stent (e.g., the upper end of the stent with reference to the illustration in FIG. 10) are connected to and integrated with respective straight-line portions 11 in the axially adjacent wavy annular member (i.e., the second wavy annular member counting from the one end or upper end of the stent) by the connection portions 3. The four instances of connection by the connection portions 3 are spaced apart at equal angular intervals (ninety degrees) from one another so that two of the connections are positioned diametrically opposite one another while the other two connections are positioned diametrically opposite one another. As further shown in FIG. 10, two of the straight-line portions 11 that are diametrically opposite one another are connected to a respective straight-line portion 11 in the third wavy annular member (i.e., the third wavy annular member counting from the one end or upper end of the stent). In this way, three straight-line portions 11 at the upper end of the stent are axially continuous with each other and integrated with each other by two connection portions 3.

Similarly, four of the straight-line portions 11 in the end-most wavy annular member at the opposite end of the stent (e.g., the lower end of the stent with reference to the illustration in FIG. 10) are connected to and integrated with respective straight-line portions 11 in the axially adjacent wavy annular member by the connection portions 3. The four instances of connection by the connection portions 3 at the opposite end of the stent are spaced apart at equal angular intervals (ninety degrees) from one another so that two of the connections are positioned diametrically opposite one another while the other two connections are positioned diametrically opposite one another. FIG. 10 illustrates that two of the straight-line portions 11 positioned diametrically opposite one another are connected to a respective straight-line portion 11 in the third wavy annular member (i.e., the third wavy annular member counting from the lower end). By virtue of this, three straight-line portions 11 at the lower end of the stent are axially continuous with each other and integrated with each other by two connection portions 3.

Except for the two wavy annular members at each axial end of the stent shown in FIG. 10, the connection portions 3 in each wavy annular members are shifted in a direction orthogonal to the axis of the stent relative to the connection portions 3 in the axially adjacent way annular member. In the illustrated embodiment, except for the two wavy annular members at each axial end of the stent, the connection portions 3 in each wavy annular member are rotationally shifted ninety degrees relative to the connection portions in the axially adjacent wavy annular member. Therefore, except for the two axial ends of the stent, there is no portion of the stent where three or more parallel straight-line portions 11 are successively connected with each other by respective connection portions. Therefore a load generated when one wavy annular member has changed its configuration to follow the deformation of a blood vessel can be inhibited or prevented from being directly (or linearly) transmitted to an non-adjacent wavy annular member, thus allowing the wavy annular members to display an individual expansion function.

The stent 1 has a plurality of connection portions 3 connecting the axially adjacent wavy annular members 2 to each other. Therefore the axially adjacent wavy annular members 2 are not spaced from each other accidentally and thus the entire stent displays a sufficient expansive force. Only one connection portion 3 may be formed between the adjacent wavy annular members 2. The length of the connection portion 3 in the axial direction of the stent 1 is preferably not more than 1.0 mm, more preferably in the range of 0.1 mm to 0.4 mm.

The stent 1 shown in FIGS. 1-4 has two connection portions 3 connecting the axially adjacent wavy annular members 2 to each other. The two connection portions 3 in each wavy annular member are located at opposed (diametrically opposite) positions. The connection portions 3 connecting axially adjacent wavy annular members 2 of the stent shown in FIGS. 1-4 are so disposed that they are not continuous with each other in the axial direction of the stent 1 (i.e., the connection portions 3 are disposed so that two or more of the connection portions are not continuous with one another). More specifically, in the stent 1 of the embodiment shown in FIGS. 1-4, the connection portions 3 connecting a first and a second axially adjacent wavy annular members are rotationally shifted relative to the axially adjacent connection portions 3 connecting the next pair of axially adjacent wavy annular members. In the illustrated embodiment, the connection portions 3 connecting a first and a second axially adjacent wavy annular members are rotationally shifted ninety degrees relative to the axially adjacent connection portions 3 connecting the second wavy annular member to the axially adjacent third wavy annular member.

After the stent 1 is formed in the developmental state shown in FIG. 4 in which the stent 1 has a relatively larger diameter as compared to when the stent 1 is in the state shown in FIGS. 1 and 2 in which the stent 1 has a relatively smaller diameter, the stent 1 is mounted on an expandable balloon of an appliance by decreasing the diameter of the stent 1. By thereafter expanding the balloon, the diameter of the stent 1 is increased to a state in which the diameter of the stent is larger than the diameter of the stent in the state shown in FIG. 4.

In the stents of all of the embodiments disclosed here, the length of the parallel straight-line portion 11 is shorter than that of the first inclined straight-line portion 12, the inclined curved line portion 13, and the second inclined straight-line portion 14. Although this length relationship is preferable, the stent is not limited to this configuration. For example, as in the case of a stent 20 shown in FIG. 8, the length of a parallel straight-line portion 11a may be almost equal to that of the first inclined straight-line portion 12, the inclined linear portion (inclined curved line portion) 13, and the second inclined straight-line portion 14. By making the length of the parallel straight-line portion 11a almost equal to that of the first inclined straight-line portion 12, the inclined linear portion (inclined curved line portion) 13, and the second inclined straight-line portion 14 as in the case of the stent 20 of this embodiment, the flexibility of the stent can be enhanced.

Figure 8:
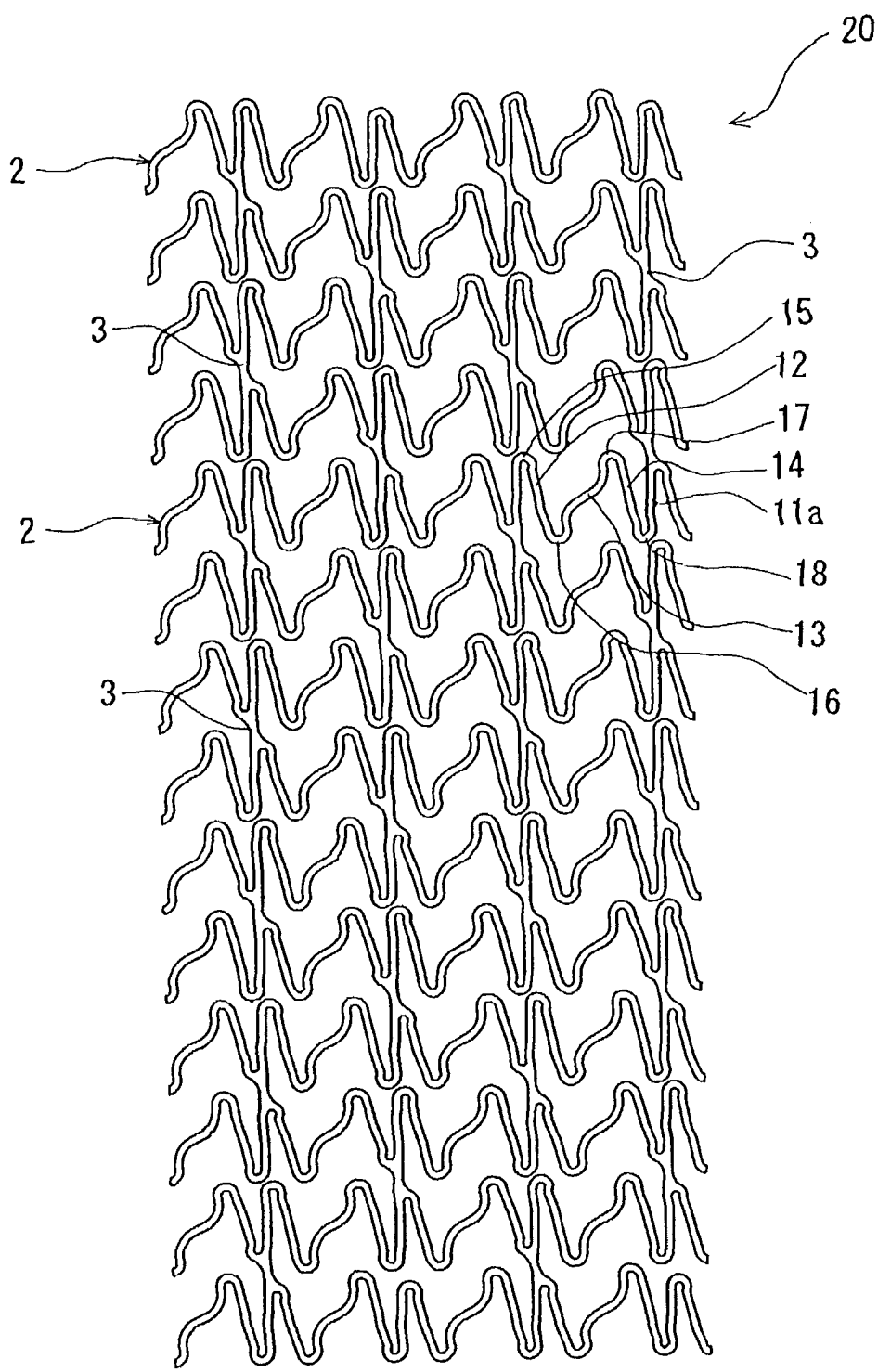
FIG. 8 is a development view, in plan, of a stent according to another embodiment disclosed here when the stent is manufactured.

In the stent 20 of this embodiment shown in FIG. 8, the one-end side bent portion 15 and the one-end side bent portion 17 (more specifically, the one-end side bent portion not connected by the connection portion) are disposed at almost the same position in the axial direction of the stent and penetrate into the adjacent wavy annular member 2 to some extent. Similarly the other-end side bent portion 16 and the other-end side bent portion 18 (more specifically, the other-end side bent portion not connected by the connection portion) are disposed at almost the same position in the axial direction of the stent and penetrate into the adjacent wavy annular member 2 to some extent. That is, except the bent portions connected by the connection portion, waves of the wavy annular member 2 have almost the same size. The wavy annular members 2 do not have projected bent portions.

Figure 9:
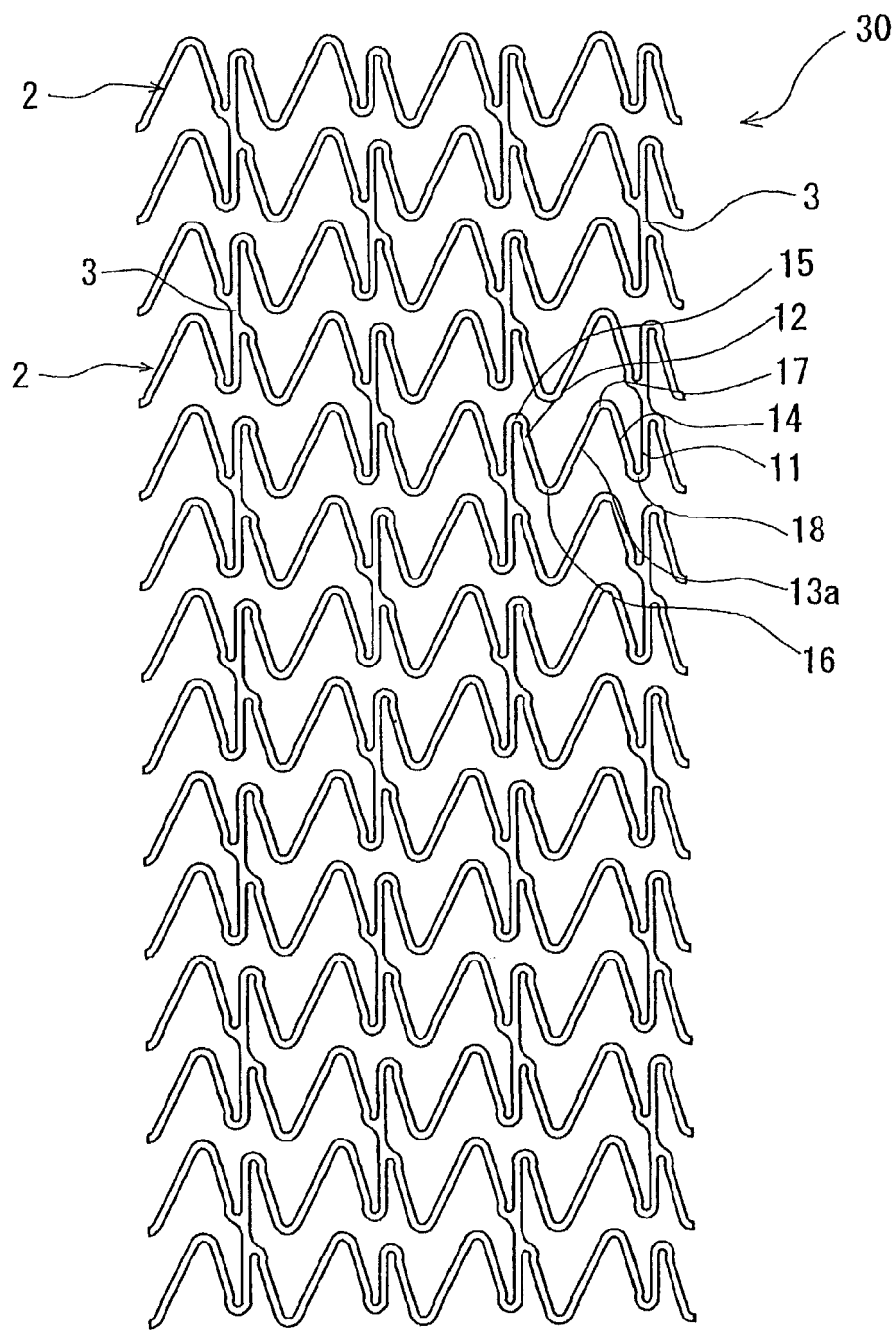
FIG. 9 is a development view, in plan, of a stent according to an additional embodiment disclosed here when the stent is manufactured.

In the stents of all the above-described embodiments, the inclined linear portion 13 is formed as an inclined curved line portion. Although this is preferable, other variations are possible. For example, as in the case of the embodiment of the stent 30 shown in FIG. 9, the inclined linear portion may be a further inclined straight-line portion (third inclined straight-line portion) 13a.

The stents of all the above-described embodiments are formed substantially as a tube and each have a diameter dimensioned so that the stent 1 can be inserted into a lumen inside a living body. The stent 1 can be expanded when a force spreading radially outward from the inside of the tube is applied. Thus, the stent 1 is a so-called balloon expandable stent. It is preferable that the material of the balloon expandable stent has a certain degree of compatibility with the living body. For example, it is possible to use stainless steel, tantalum or tantalum alloys, platinum or platinum alloys, gold or gold alloys, cobalt based alloys, a cobalt-chrome alloy, a titanium alloy, and a niobium alloy. It is preferable to plate the stent with a noble metal such as gold and platinum after the stent is fabricated into a final shape. As the stainless steel, SUS 316L most corrosion-resistant is preferably used.

It is preferable to anneal the stent after it is fabricated into the final shape. Annealing improves the flexibility and plasticity of the entire stent. Thereby the stent can be favorably implanted at a curved portion of a blood vessel. As compared with a non-annealed stent, the annealed stent has a lower force of restoring to an original state after it is expanded, and especially has a lower force of restoring to an original linear state when it is expanded at the curved portion of the blood vessel. This helps minimize physical stimulation to the inner wall of the curved portion of the blood vessel, thus reducing the cause of a recurrence of stenosis. It is preferable to anneal the stent by heating it to 900° C. to 1200° C. in an inert gas atmosphere (e.g., a mixture gas of nitrogen and hydrogen), so that no oxide film is formed on the surface of the stent, and then slowly cooling it. The stent has a diameter preferably 0.8 mm to 1.8 mm, more preferably 0.9 mm to 1.6 mm in an unexpanded state. The stent 1 preferably has a length of 8 mm to 40 mm in an unexpanded state. It is preferable that each wavy annular members 2 has a length of 8 mm to 25 mm.

The stent is shaped by removing portions other than a frame structure from a tube (more specifically, metal pipe). More specifically, the stent is formed by removing unnecessary portions from the metal pipe by an etching process, known as photo-fabrication, using masks and chemicals; electric discharge machining using a die; and cutting processing (for example, mechanical polishing, laser cutting processing). In addition, it is preferable to polish edges of the frame structure by chemical polishing or electrolytic polishing after the frame structure is formed.

The stent of the present invention may be coated with a material suitable for use with a living body. The stent may be coated on its inner surface, outer surface or inner and outer surfaces. As the material suitable for the living body, synthetic resin and metal suitable for the living body can be used. The following inactive metals are used to coat the surface of the stent: gold by an electroplating method, stainless steel by an evaporation method, silicon carbide, diamond-like carbon, plated titanium nitride, and plated gold by a sputtering method. As the synthetic resin, the following thermoplastic resins or thermosetting resins can be used: polyolefin (for example, polyethylene, polypropylene, ethylene-propylene copolymer), polyvinyl chloride, ethylene-vinyl acetate copolymer, polyamide elastomer, polyurethane, polyester, fluorocarbon resin, silicone resin. It is preferable to use polyolefin, polyamide elastomer, polyester, polyurethane, silicone resin. A resin decomposable in the living body (polylactic acid, polyglycolic acid, polylactic acid-poly glycolic acid copolymer) is also favorable. It is preferable that a film of the synthetic resin is soft to such an extent as not to prevent a frame constituting the stent from being curved. The thickness of the film of the synthetic resin is set favorably to the range of 3 μm to 300 μm and more favorably in the range of 5 μm to 100 μm.

As the method of thinly coating the surface of the stent with the synthetic resin, it is possible to use a method of inserting the stent into the melted synthetic resin or into the synthetic resin dissolved in a solution. It is also possible to use a chemical evaporation method involving polymerizing a monomer over the surface of the pipe made of the super-elastic metal. In the case where the surface of the stent is coated very thinly with the synthetic resin, the use of a dilute solution or the chemical evaporation method is preferable. To improve the quality of the material suitable for the living body to a higher extent, the resinous film may be coated with an anti-thrombus material or the anti-thrombus material may be fixed to the resinous film. As the anti-thrombus material, known various resins can be used singly or as a mixture thereof. For example, polyhydroxyethyl methacrylate, a copolymer of hydroxyethyl methacrylate and styrene (for example, HEMA-St-HEMA block copolymer) can be preferably used.

An embodiment of the stent delivery device disclosed here is now described with reference to the illustration in FIGS. 11-13. A stent delivery device 100 includes (i.e., comprises) a tubular shaft body 102, a foldable and expandable balloon 103 disposed at the distal end of the shaft body 102, and a stent 101 mounted on the folded balloon 103, with the stent 101 covering the balloon 103. The stent 101 is expanded by virtue of expansion of the balloon 103.

Figure 11:
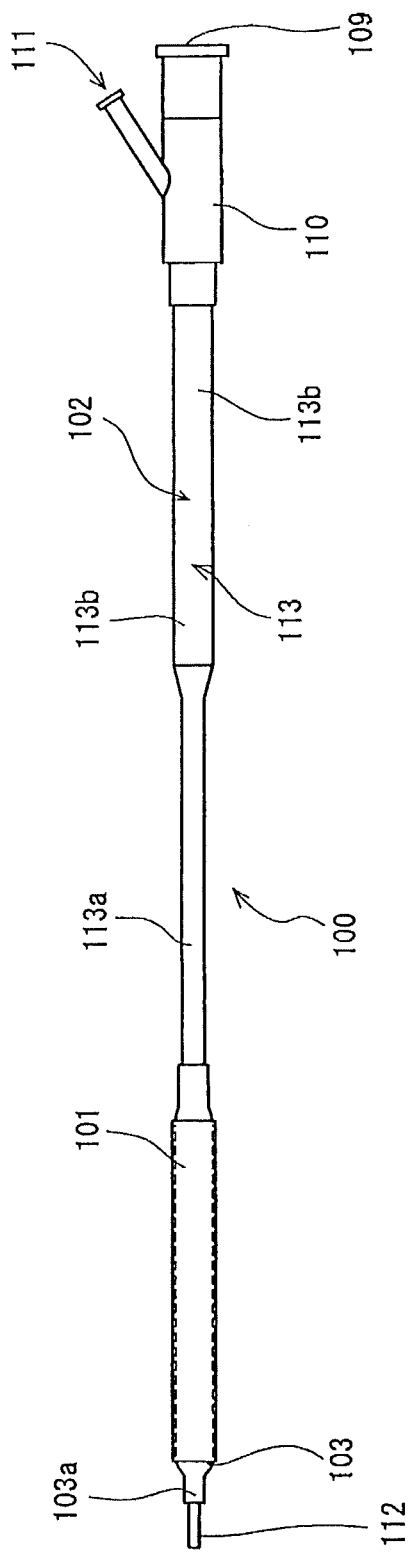
FIG. 11 is a front view of a stent delivery device according to one embodiment disclosed here.
Figure 12:
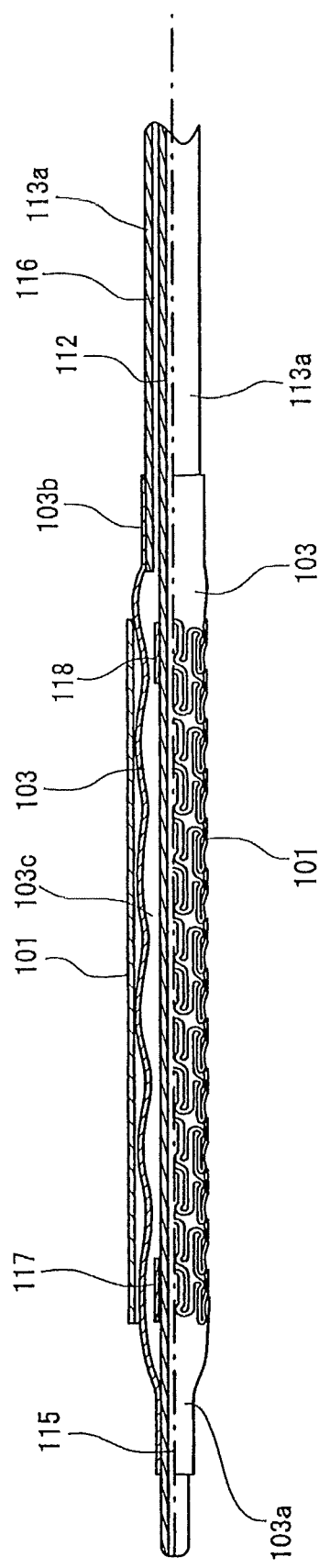
FIG. 12 is an enlarged cross-sectional view of a distal portion of the stent delivery device shown in FIG. 11.

Similar to the above-described stent 1, the stent 101 shown in FIGS. 11 and 12 is formed substantially as a tube and possesses a form in which plural wavy annular members 2 are arranged adjacent to each other in the axial direction of the stent 101, with axially adjacent wavy annular members 2 connected to each other. The stent 101 also has a diameter whose dimension is so set that the stent 101 can be inserted into a lumen inside a living body, and can be expanded when a force spreading radially outwardly from inside the tube is applied. The wavy annular member 2 has parallel straight-line portions 11 extending in parallel with the axis of the stent 101 before and after the stent 101 expands. The stent 101 includes connection portions 3 each connecting ends of the parallel straight-line portions 11 of the adjacent wavy annular members 2 to one another.

As the stent of the blood vessel expansion appliance, an expandable stent, namely a so-called balloon expandable stent can be used. This stent can be a stent having a diameter dimensioned so that the stent is positionable in a lumen inside a living body and expandable when a force spreading radially outward from the inside of the tube is applied.

As the stent 101, it is possible to use any of the embodiments of the stent described above. More specifically, the stent 101 can be any of the stents 1, 10, 20, 30, 40 shown in FIGS. 1-10 and described above. It is preferable that the area of the wavy element of the stent is 60% to 80% of the area of the peripheral surface of the stent including vacant spaces when the stent is mounted on the balloon 103. The shaft body 102 of the blood vessel expansion appliance 100 disclosed here includes a balloon expansion lumen whose one end communicates with the inside of the balloon 103. The stent delivery device 100 has a radiographing member fixed to the outer surface of the shaft body 102 at a position corresponding to the center of the stent, or two radiographing members fixed to the outer surface of the shaft body 102 at positions corresponding to one end and the other end of the central portion of the stent having a predetermined length.

As shown in FIG. 11, the shaft body 102 of the stent delivery device 100 of this embodiment has a guide wire lumen 115 whose one end is open at a front end of the shaft body 102 and whose other end is open at a rear end of the shaft body 102. The guide wire lumen is thus a through hole.

The stent delivery device 100 includes the tubular shaft body 102, the stent-expanding balloon 103 attached to the front end of the shaft body 102; and the stent 101 mounted on the balloon 3. The shaft body 102 has an inner tube 112, an outer tube 113, and a branch hub 110.

As shown in FIG. 12, the inner tube 112 is outfitted with the guide wire lumen 115 into which a guide wire is insertable. The length of the inner tube 112 is preferably 100 mm to 2000 mm, more preferably 150 mm to 1500 mm. The outer diameter of the inner tube 112 is preferably 0.1 mm to 1.0 mm and more preferably 0.3 mm to 0.7 mm. The thickness of the inner tube 112 is preferably 10 µm to 150 µm, more preferably 20 µm to 100 µm. The inner tube 112 is inserted into the outer tube 113 to such an extent that the front end of the inner tube 112 projects out from the outer tube 113 and distally beyond the distal end of the outer tube 113. A balloon-expanding lumen 116 is formed between the outer surface of the inner tube 112 and the inner surface of the outer tube 113, and has a relatively large volume. The front end of the outer tube 113 into which the inner tube 112 is inserted is located a little rearward from the front end of the inner tube 112.

The length of the outer tube 113 is preferably 100 mm to 2000 mm and more preferably 150 mm-1500 mm. The outer diameter of the outer tube 113 is preferably 0.5 mm to 1.5 mm, more preferably 0.7 mm to 1.1 mm. The thickness of the outer tube 113 is preferably 25 µm to 200 µm, more preferably 50 µm to 100 µm.

In the stent delivery device 100 of this embodiment, the outer tube 113 is composed of a front-end side outer tube 113a and a shaft-body side outer tube 113b joined with the front-end side outer tube 113a. The diameter of the front-end side outer tube 113a decreases taperingly in the region forward from the joining position at which the front-end side outer tube 113a and the shaft body side outer tube 113b are joined with each other. The diameter of a portion of the front-end side outer tube 113a forward from the tapered region has a small diameter.

The outer diameter of the front-end side outer tube 113a at its smaller-diameter portion is preferably 0.50 mm to 1.5 mm and more preferably 0.60 mm to 1.1 mm. The outer diameter of the front-end side outer tube 113a at its rear end and that of the shaft-body side outer tube 113b are preferably 0.75 mm to 1.5 mm, more preferably 0.9 mm to 1.1 mm.

Figure 13:
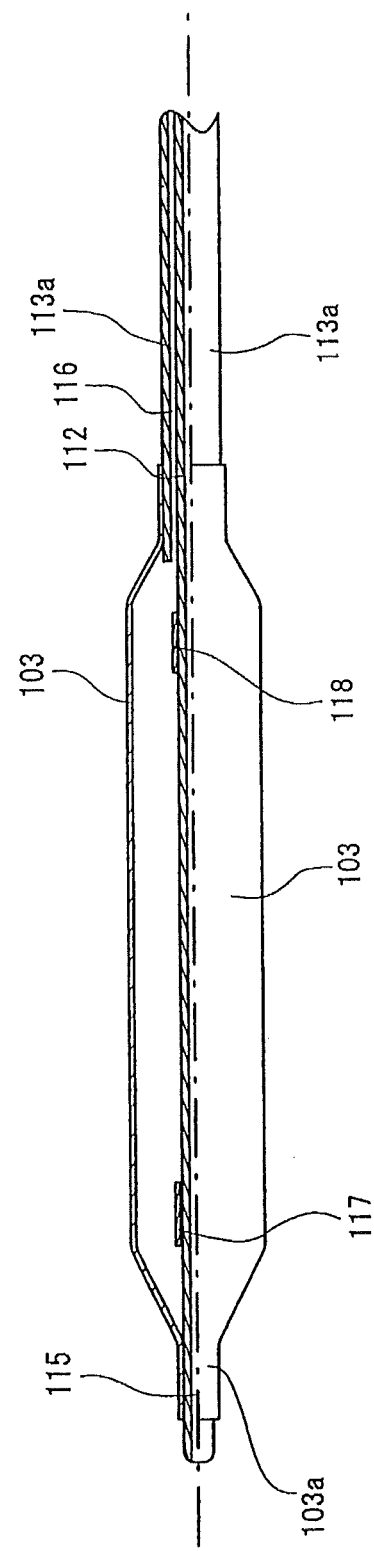
FIG. 13 is a front view of a portion of the stent delivery device for purposes of explaining the operation.

The balloon 103 has a front-end side bonding portion 103a noted in FIGS. 11-13 and a rear-end side bonding portion 103b noted in FIG. 12. The front-end side bonding portion 103a is fixed to the inner tube 112 at a position a little rearward from the front end of the inner tube 112. The rear-end side bonding portion 103b is fixed to the front end of the outer tube 113. The balloon 103 communicates with the balloon-expanding lumen 116 at a position in the vicinity of the proximal end of the balloon.

A material having a certain degree of flexibility is preferably used for the inner tube 112 and the outer tube 113. It is preferable to use thermoplastic resins such as polyolefin (for example, polyethylene, polypropylene, ethylene-propylene copolymer, ethylene-vinyl acetate copolymer), polyvinyl chloride, polyamide elastomer, and polyurethane; silicone rubber; and latex rubber. It is more preferable to use the thermoplastic resins. Polyolefin is most preferably of the thermoplastic resins. As shown in FIG. 12, the balloon 103 is foldable. When the balloon 103 is not expanded, it can be folded over the outer surface of the inner tube 112. As shown in FIG. 13, the balloon 103 has a tubular (preferably, cylindrical) expandable portion having an approximately uniform diameter so that it is possible to expand the stent 101 to be mounted on the balloon 103. The expandable portion is not necessarily cylindrical but may be polygonal. As described above, the front-end side bonding portion 103a of the balloon 103 is bonded in a liquid-tight manner to the inner tube 112, and the rear-end side bonding portion 103b is bonded in a liquid-tight manner to the front end of the outer tube 113 with an adhesive agent or by thermal fusion. The balloon 103 includes tapered portions between the central expandable portion and each of the bonding portions 103a, 103b as shown in FIG. 13.

An expansion space 103c is formed between the inner surface of the balloon 103 and the outer surface of the inner tube 112. The entire circumference of the expansion space 103c communicates with the balloon-expanding lumen 116 at the rear end of the expansion space 103c. Because the expansion space 103c communicates with the balloon-expanding lumen 116 having a comparatively large volume, it is relatively easy to inject an expansion fluid into the balloon 103 through the balloon-expanding lumen 116.

Materials having a certain degree of flexibility are preferably used for the balloon 103. It is preferable to use thermoplastic resins such as polyolefin (for example, polyethylene, polypropylene, ethylene-propylene copolymer, ethylene-vinyl acetate copolymer, crosslinked ethylene-vinyl acetate copolymer), polyvinyl chloride, polyamide elastomer, polyurethane, polyester (for example, polyethylene terephthalate), polyarylane sulfide (for example, polyphenylene sulfide), silicone rubber, and latex rubber. It is particularly preferable to use an extensible material. A biaxially oriented material is preferably used for the balloon 103 because of its high degree of strength and expansion.

Regarding the size of the balloon 103, the outer diameter of the expanded cylindrical portion (expandable portion) thereof is preferably in the range of 2 mm to 4 mm, more preferably 2.5 mm to 3.5 mm. The length of the balloon 103 is preferably in the range of 10 mm to 50 mm, more preferably in the range of 20 mm to 40 mm. The outer diameter of the front-end side bonding portion 103a is preferably in the range of 0.9 mm to 1.5 mm, more preferably in the range of 1 mm to 1.3 mm. The length of the front-end side bonding portion 103a is preferably in the range of 1 mm to 5 mm, and more preferably 1 mm to 1.3 mm. The outer diameter of the rear-end side bonding portion 103b is preferably in the range of 1 mm to 1.6 mm, more preferably 1.1 mm to 1.5 mm. The length of the rear-end side bonding portion 103b is preferably in the range of 1 mm to 5 mm, more preferably in the range of 2 mm to 4 mm. As shown in FIG. 12, the blood vessel expansion appliance 100 has two radiographing members 117, 118 fixed to the outer surface of the shaft body 102 at positions corresponding to opposite ends of the cylindrical portion (expandable portion) of the stent, when the stent is expanded. Further, the blood vessel expansion appliance 100 may have two radiographing members fixed to the outer surface of the shaft body (in this embodiment, the outer surface of the inner tube 112) 102 at positions corresponding to the opposite ends of the central portion of the stent 101 having a predetermined length. Further the blood vessel expansion appliance 100 may have one radiographing member fixed to the outer surface of the shaft body 102 at a position corresponding to the central portion of the stent 101.

The radiographing members 117, 118 are preferably in the shape of a ring having a predetermined length or a coiled wire. It is preferable that the radiographing members 117, 118 are made of gold, platinum, tungsten or alloys thereof or a silver-palladium alloy.

The stent 101 is mounted on the balloon 103, with the stent covering the folded balloon 103. The stent is formed by processing a metal pipe (metal tubular member) having an inner diameter smaller than the inner diameter of the stent at the time when the stent is expanded and larger than the outer diameter of the folded balloon. The balloon is inserted into the formed stent, and a force is uniformly applied to the outer surface of the stent to decrease the diameter of the stent. In this manner, the production of the stent is completed. That is, production of the stent 101 is completed when the stent 101 is mounted on the balloon by compressing the stent. A linear rigidity-imparting member may be inserted between the inner tube 112 and the outer tube 113, namely into the balloon-expanding lumen 116. The rigidity-imparting member prevents excess bending of the body 102 of the stent delivery device 100 at bent portions of blood vessels without much deteriorating the flexibility of the stent delivery device 100 and facilitates the insertion of the frond end of the stent delivery device 100 into the bent portions of blood vessels. It is preferable that the diameter of the front end of the rigidity-imparting member is set smaller than those of the other portions of the rigidity-imparting member by grinding or the like. It is preferable that front end of the small-diameter portion of the rigidity-imparting member extends to the vicinity of the front end of the outer tube of the body of the stent delivery device 100. It is also preferable that the rigidity-imparting member consists of a metal wire having a diameter of 0.05 mm to 1.50 mm, more preferably 0.10 mm to 1.00 mm. The rigidity-imparting member 133 is preferably made of an elastic metal such as stainless steel or a super elastic alloy and more preferably high-strength stainless steel for a spring or a wire of the super elastic alloy.

As shown in FIG. 11, the stent delivery device 100 of this embodiment has a branched hub 110 fixed to the rear end of the device. The branched hub 110 has an inner-tube hub, fixed to the inner tube 112, which has a guide wire introducing opening 109 and which communicates with the guide wire lumen 115 and forming a guide wire port; and an outer-tube hub, fixed to the outer tube 113, which communicates with the balloon-expanding lumen 116 and has an injection port 111. The outer-tube hub and the inner-tube hub are fixed to each other. As the material of the branched hub 110, thermoplastic resin such as polycarbonate, polyamide, polysulfone, polyacrylate, and methacrylate-butylene-styrene copolymer is preferably used. The construction of the stent delivery device is not limited to the above-described construction. For example, the stent delivery device may have a guide wire insertion opening, communicating with the guide wire lumen, disposed at a central portion thereof.

In the stent disclosed here by way of a number of embodiments, the wavy annular member has the parallel straight-line portions extended in parallel with the axis of the stent before and after the stent expands. Therefore it is possible to restrain the axial length of the stent from becoming short when the stent expands. Further before and after the stent expands, the connection portion connects ends of the parallel straight-line portions kept in parallel with the axis of the stent. Therefore it is possible to prevent the apexes of the bent portions of the adjacent wavy annular members and thus improve the flexibility (follow-up performance for organs) when the stent contracts and expands, It is also possible to provide the stent with a sufficient force of expanding organs when the stent expands and in addition uniformly expand the stent.

The principles, embodiments and modes of operation of the stent disclosed here have been described in the foregoing specification, but the invention which is intended to be protected is not to be construed as limited to the particular embodiments disclosed. The embodiments described herein are to be regarded as illustrative rather than restrictive. Variations and changes may be made by others, and equivalents employed, without departing from the spirit of the present invention. Accordingly, it is expressly intended that all such variations, changes and equivalents which fall within the spirit and scope of the present invention as defined in the claims, be embraced thereby.

What is claimed is:

1. A stent possessing an axis, formed substantially as a tube and comprising a plurality of wavy annular members arranged along an axial extent of the stent so that the plurality of wavy annular members are axially adjacent wavy annular members, with axially adjacent wavy annular members connected to each other, the axially adjacent annular members being configured so that the stent in a first state possesses a relatively smaller outer diameter dimensioned to be inserted into a lumen inside a living body, and is expandable from the first state to a second expanded state possessing a relatively larger outer diameter when a force spreading radially outwardly from inside the tube is applied to the stent, each of the plurality of wavy annular members comprising a plurality of modified M-shaped linear portions which are continuous with each other, each of the modified M-shaped linear portions including four linear portions, the four linear portions comprising: i) a straight-line portion extending parallel to the axis of the stent when the stent is in the first state; ii) a first inclined straight-line portion connected to one end of the straight-line portion through a bent portion and oriented obliquely to the axis of the stent at least when the stent is in the expanded second state; iii) an inclined curved line portion connected to one end of the first inclined straight-line portion through a bent portion and extending obliquely to the axis of the stent; and iv) a second inclined straight-line portion connected to one end of the inclined curved linear portion through a bent portion and oriented obliquely to the axis of the stent at least when the stent is in the expanded second state.

2. A stent according to claim 1, wherein the inclined curved line portion of each of the modified M-shaped linear portions includes two curved portions which curve in opposite directions.

3. A stent according to claim 1, wherein the first inclined straight-line portion and the second inclined straight-line portion extend parallel to the axis of the stent when the stent is in the first state before the stent is expanded to the expanded second state.

4. A stent according to claim 1, wherein the inclined curved line portion extends obliquely to the axis of the stent when the stent is in the first state before the stent is expanded to the expanded second state, and wherein the inclined curved line portion extends obliquely to the axis of the stent after the stent is expanded to the expanded second state.

5. A stent according to claim 1, further comprising connection portions each connecting together opposed ends of the straight-line portions of the axially adjacent wavy annular members.

* * * * *